United States Patent [19]

Malherbe et al.

[11] 4,230,722
[45] Oct. 28, 1980

[54] DIHALOVINYLCYCLOPROPANETHIOLIC ACID ESTERS AND THEIR USE IN PEST CONTROL

[75] Inventors: Roger Malherbe, Muttenz; Daniel Bellus, Riehen; Laurenz Gsell, Basel, all of Switzerland

[73] Assignee: Ciba-Geigy Corporation, Ardsley, N.Y.

[21] Appl. No.: 49,367

[22] Filed: Jun. 18, 1979

[30] Foreign Application Priority Data

Jun. 26, 1978 [CH] Switzerland .......................... 6935/78
May 11, 1979 [CH] Switzerland .......................... 4414/79

[51] Int. Cl.³ .................. A01N 37/14; C07C 153/023
[52] U.S. Cl. .................................. 424/301; 260/455 R
[58] Field of Search ...................... 260/455 R; 424/301

[56] References Cited

U.S. PATENT DOCUMENTS

| | | | |
|---|---|---|---|
| 2,408,094 | 9/1946 | Pavlic | 260/455 R |
| 3,900,507 | 8/1975 | Karrer et al. | 260/455 R |
| 3,996,244 | 12/1976 | Fujimoto et al. | 260/455 R |

FOREIGN PATENT DOCUMENTS 2615435  4/1976  Fed. Rep. of Germany ...... 260/455 R

*Primary Examiner*—Henry R. Jiles
*Assistant Examiner*—Robert C. Whittenbaugh
*Attorney, Agent, or Firm*—John J. Maitner

[57] ABSTRACT

Dihalovinylcyclopropanethiolic acid esters of the formula

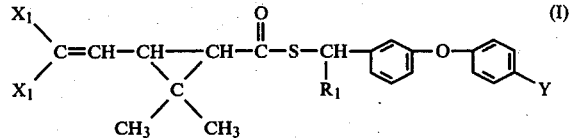

wherein $X_1$ represents fluorine, chlorine or bromine, $R_1$ represents hydrogen, methyl, ethynyl or cyano, and Y represents hydrogen, fluorine, chlorine or bromine, processes for their manufacture, and a method of controlling pests which comprises the use of these compounds.

10 Claims, No Drawings

DIHALOVINYLCYCLOPROPANETHIOLIC ACID ESTERS AND THEIR USE IN PEST CONTROL

The present invention relates to dihalovinylcyclopropanethiolic acid esters, processes for their manufacture, and a method of controlling pests which comprises the use of these compounds.

The dihalovinylcyclopropanethiolic acid esters have the formula

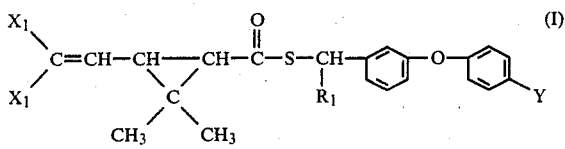

wherein $X_1$ represents fluorine, chlorine or bromine, $R_1$ represents hydrogen, methyl, ethynyl or cyano, and Y represents hydrogen, fluorine, chlorine or bromine.

Preferred compounds on account of their action are those of the formula I, wherein $X_1$ represents chlorine, $R_1$ represents hydrogen, methyl, ethynyl or cyano, and Y represents hydrogen.

The compounds of the formula I are obtained by methods which are known per se, for example as follows:

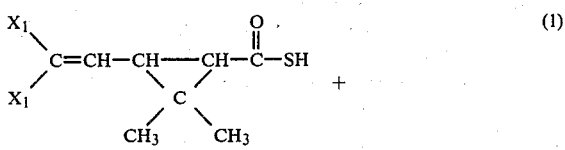

(II)

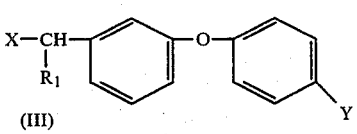

(III)

$$\xrightarrow{\text{acid acceptor}} \text{I} \quad (1)$$

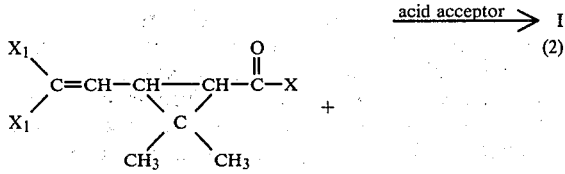

(IV)

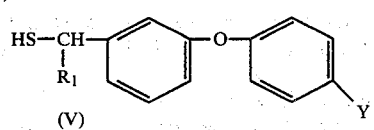

(V)

$$\xrightarrow{\text{acid acceptor}} \text{I} \quad (2)$$

In the formulae II to V, $R_1$, $X_1$, and Y are as defined for formula I and X represents a halogen atom, in particular a chlorine or bromine atom.

Suitable acid acceptors are in particular tertiary amines, such as trialkylamines and pyridine, and also hydroxides, oxides, carbonates and bicarbonates of alkali metals and alkaline earth metals, and also alkali metal alcoholates, for example potassium tert-butylate and sodium methylate. Processes 1 and 2 are carried out at a reaction temperature between $-10°$ and $120°$ C., usually between $20°$ and $80°$ C., under normal pressure and preferably in an inert solvent or diluent. Examples of suitable solvents or diluents are: ether and ethereal compounds, for example diethyl ether, dipropyl ether, dioxane, dimethoxyethane and tetrahydrofurane; amides, such as N,N-dialkylated carboxyamides; aliphatic, aromatic and halogenated hydrocarbons, especially benzene, toluene, xylenes, chloroform and chlorobenzene; nitriles, such as acetonitrile; dimethyl sulfoxide.

The starting materials of the formulae III and IV are known, whilst those of the formulae II and V are new. All these starting materials, however, can be prepared by methods analogous to known ones.

The compounds of the formula I are in the form of a mixture of different optically active isomers if individual optically active starting materials are not used in the reaction. The different isomer mixtures can be separated into the individual isomers by known methods. The compound of the formula I is to be understood as comprising both the individual isomers and the mixtures thereof. The compounds of the formula I are suitable for controlling a variety of animal and plant pests. In particular, the compounds of the formula I are suitable for controlling insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

In particular, the compounds of the formula I are suitable for controlling insects which are harmful to plants, especially insects which damage plants by eating, in ornamentals and crops of useful plants, especially in cotton plantations (e.g. Spodoptera littoralis and Heliothis virescens) and in vegetable crops (for example Leptinotarsa decemlineata and Myzus persicae).

The active compounds of the formula I also have a very good action against flies, for example Musca domestica, and mosquito larvae.

The acaricidal and/or insecticidal action can be substantially broadened and adapted to prevailing circumstances by addition of other insecticides and/or acaricides. Examples of suitable additives include: organic phosphorus compounds, nitrophenols and derivatives thereof, formamidines, ureas, pyrethroids, carbamates, and chlorinated hydrocarbons.

Compounds of the formula I are also combined with particular advantage with substances which exert a synergistic or potentiating effect on pyrethroids. Examples of such compounds include: piperonyl butoxide, propynyl ether, propynyl oximes, propynyl carbamates and propynyl phosphates, 2-(3,4-methylenedioxyphenoxy)-3,6,9-trioxaundecane (Sesamex or Sesoxane), S,S,S,-tributylphosphorotrithioate, 1,2-methylenedioxy-4(2-(octylsulfinyl)-propyl)-benzene.

The compounds of the formual I also have very good action against Lepidoptera that feed on keratin, for example Tineola spec. and Tinea spec., and also against Coleoptera that feed on keratin, for example Anthrenus spec. and Attagenus spec. The compounds are therefore very suitable for protecting keratinous material against attack by pests. They can be applied by the methods commonly employed in textile finishing and in particular provide such material with a wash- and lightfast protective finish against feeding damage by insects.

The keratinous material to be protected can be both in the raw and in the processed state, for example raw or processed sheep's wool, products made of other animal hairs, hides, furs and feathers. In addition to the light- and washfast finish in the dyebath and in pad application, the compounds of the formula I can also be used for impregnating wool and woollen articles in dry cleaning, whereby excellent protection against damage by eating is also afforded.

In addition to their insecticidal action, the compounds of the formula I act against the larvae of the webbing cloths moth (Tineola bisselliella and of the common clothes moth (Tineola pellionella) as well as against the larvae of the fur beetle and carpet beetle (Attagenus spec. and Anthrenus spec. respectively). The textiles, such as blankets, wool carpets, woollen underwear, woollen clothing and knits, are therefore protected against the common pests that feed on keratin. The materials to be protected also include blends, one component of which is wool, for example blends of wool and other natural fibres such as cotton, and of wool and synthetic fibres.

The compositions employed for protecting keratinous material against feeding damage will contain the compounds of the formula I in dissolved or dispersed form. Solutions, suspensions and emulsions of the active substances are therefore used.

Because of their good solubility in organic solvents, the compounds of the formula I are also particularly suitable for application from non-aqueous media. The material to be protected can either be simply impregnated with these solutions, or the moth- and beetle-proof finish can be combined with a dry cleaning process by choosing a suitable solvent.

Particularly suitable organic solvents are propylene glycol, methoxyethanol, ethoxyethanol and dimethyl formamide, to which dispersing agents and/other assistants can be added. Suitable dispersing agents are emulsifiers, for example sulfated castor oil, sulfite waste liquor and fatty alcohol sulfates.

The compounds of the formula I are also most suitable for spray application, as they are very readily soluble in the conventionally employed organic, readily volatile solvents. Wool-containing textiles, furs and feathers are particularly suitable for spray application.

Particularly preferred methods of application are those such as padding, impregnating and spraying with volatile organic solvents, as pollution of the wastewaters is avoided on account of the recovery of the solvent.

The compounds of the formula I can also be used in combination with other protectants which act against insects that feed on keratin, for example urea derivatives, benzimidazoles, aromatic sulfonamides and phosphates and phosphonates.

The compounds of the formula I may be used as pure active substance or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners, binders and/or fertilisers.

The compositions of the present invention are manufactured in known manner by homogeneously mixing and/or grinding active substances of the formula I with the suitable carriers, with or without the addition of dispersants or solvents which are inert to the active substances.

The compounds of the formula I may be processed to the following formulations:

Solid formulations

Dusts, tracking powders and granules (coated granules, impregnated granules and homogeneous granules).

Liquid formulations:
(a) active substances which are dispersable in water: wettable powders, pastes and emulsions;
(b) solutions.

The content of active substance in the above described compositions is generally between 0.1% and 95%, though concentrations of up to 99.5% or even pure active substance can also be used if the compositions are applied from an aircraft or other appropriate application devices.

The compounds (active substances) of the formula I can, for example, be formulated as follows (throughout the present specification all parts and percentages are by weight):

Dusts

The following substances are used to formulate (a) a 5% and (b) a 2% dust:
(a)
  5 parts of active substance,
  95 parts of talc;
(b)
  2 parts of active substance,
  1 part of highly disperse silicic acid,
  97 parts of talc.

The active substance is mixed with the carriers and ground.

Granules

The following substances are used to formulate 5% granules:
  5 parts of active substance
  0.25 parts of epichlorohydrin,
  0.25 parts of cetyl polyglycol ether,
  3.50 parts of polyethylene glycol,
  91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo.

Wettable powders

The following constituents are used to formulate (a) a 40%, (b) and (c) a 25%, and (d) a 10% wettable powder:
(a)
  40 parts of active substance,
  5 parts of sodium dibutylnaphthalenesulfonate,
  54 parts of silicic acid.
(b)
  25 parts of active substance,
  4.5 parts of calcium ligninsulfonate,
  1.9 parts of Champagne chalk/hydroxyethyl cellulose mixture (1:1),
  1.5 parts of sodium dibutylnaphthalenesulfonate,
  19.1 parts of silicic acid,
  19.5 parts of Champagne chalk,
  28.1 parts of kaolin,
(c)
  25 parts of active substance,
  2.5 parts of isooctylphenoxy-polyoxyethyleneethanol, 1.7 parts of Champagne chalk/hydroxyethyl cellulose mixture (1:1),
8.3 parts of sodium aluminium silicate,
16.5 parts of kieselguhr,
46 parts of kaolin;
(d)
10 parts of active substance,
3 parts of a mixture of the sodium salts of saturated fatty alcohol sulfates,
5 parts of naphthalenesulfonic acid/formaldehyde condensate,
82 parts of kaolin.

The active substances are homogeneously mixed with the additives in suitable mixers and the mixture is then ground in appropriate mills and rollers. Wettable powders are obtained which can be diluted with water to give suspensions of the desired concentration.

Emulsifiable concentrates

The following substances are used to formulate (a) a 10%, (b) a 25% and (c) a 50% emulsifiable concentrate:
(a)
10 parts of active substance,
3.4 parts of expoxidised vegetable oil,
3.4 parts of a combination emulsifier consisting of fatty alcohol polyglycol ether and alkylarylsulfonate/calcium salt,
40 parts of dimethyl formamide,
43.2 parts of xylene;
(b)
25 parts of active substance,
2.5 parts of epoxidised vegetable oil,
10 parts of alkylarylsulfonate/fatty alcohol polyglycol ether mixture,
5 parts of dimethyl formamide,
57.5 parts of xylene;
(c)
50 parts of active substance,
4.2 parts of tributylphenol-polyglycol ether,
5.8 parts of cylcium dodecylbenzenesulfonate,
20 parts of cyclohexanene,
20 parts of xylene.

By diluting these concentrates with water it is possible to obtain emulsions of the required concentration.

Sprays

The following ingredients are used to formulate (a) a 5% spray, and (b) a 95% spray:
(a)
5 parts of active substance,
1 part of epichlorohydrin,
94 parts of ligroin (boiling range 160°–190° C.);
(b)
95 parts of active substance,
5 parts of epichlorohydrin.

The invention is further illustrated by the following Examples.

EXAMPLE 1

(a) Manufacture of cis-2,2-dimethyl-3-dichlorovinyl-1-cyclopropanethiolcarboxylic acid While taking care to avoid an exothermic reaction, 11.4 g of cis-2,2-dimethyl-3-dichlorovinyl-1-cyclopropanecarboxylic acid chloride are added in small amounts to an alcoholic potassium hydrogensulfide solution (prepared by saturating a solution of 19.2 g of potassium hydroxide in 10 ml of water and 180 ml of ethyl alcohol with hydrogen sulfide). After it has stood for 1 hour, the reaction mixture is poured into water and made alkaline. Neutral by-products are removed by extraction with ether. While carefully avoiding an exothermic reaction, the batch is then acidified and the thiolic acid is isolated by extraction with ether, affording the compound of the formula

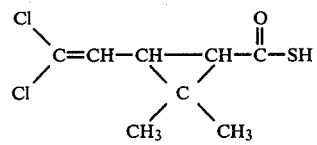

in the form of a yellow oil which is used as such in the ester synthesis.

(b) Manufacture of cis-2,2-dimethyl-3-dichlorovinyl-1-cyclopropanecarboxylic acid S-m-phenoxy-α-cyanobenzylthioate 1.65 ml of triethylamine in 5 ml of ethyl are added dropwise at 10° C. to a solution of 2.9 g of cis-2,2-dimethyl-3-dichlorovinyl-1-cyclopropanethiolcarboxylic acid and 2.9 g of m-phenoxy-α-bromobenzylcyanamide in 40 ml of hexane/ethyl ether (1:1). The mixture is stirred for 1 hour at room temperature and the organic phase is washed with water, 2 N sodium hydroxide, 2 N sulfuric acid, saturated sodium chloride solution, and dried over magnesium sulfate. The solvent is evaporated off and the residue is chromatographed over silica gel, affording the compound of the formula

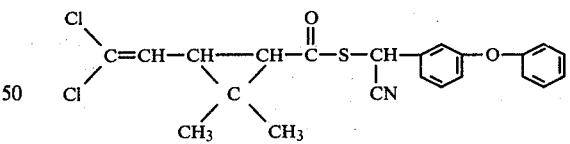

with a refractive index of $n_D^{20°} = 1.5952$.

The following compounds are also obtained in analogous manner:

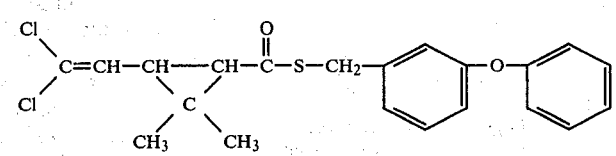

$n_D^{20°} = 1,5768$

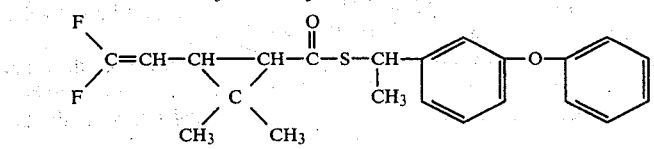

$n_D^{20°} = 1,5569$

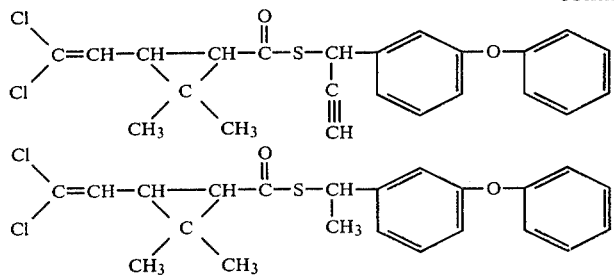

$n_D^{20°} = 1.5869$ $n_D^{20°} = 1.5896$ (c) Manufacture of m-phenoxybenzylmercaptan A solution of 30.8 g of m-phenoxybenzyl bromide in 70 ml of isopropanol is reacted with 9.5 g of thiourea in 30 ml of water and the reaction mixture is refluxed briefly. After cooling, 25 ml of a 25% ammonia solution are added and the mixture is heated briefly to reflux and then allowed to cool, whereupon it is acidified with 18% hydrochloric acid and extracted with methylene chloride. The extract is dried over magnesium sulfate and concentrated, affording the compound of the formula

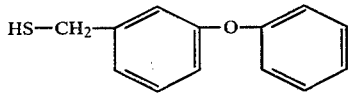

with a boiling point of 114°–116° C./0.05 mm Hg.

EXAMPLE 2: Insecticidal stomach poison action

Cotton plants were sprayed with a 0.05% aqueous emulsion of active substance (obtained from a 10% emulsifiable concentrate). After the spray coating had dried, the cotton plants were populated with Spodoptera littoralis and Heliothis virescens in the $L_3$-stage. The test was carried out at 24° C. and 60% relative humidity. In this test, the compounds of Example 1 exhibited a good insecticidal stomach poison action against Spodoptera and Heliothis larvae.

EXAMPLE 3: Acaricidal action

Twelve hours before the test for acaricidal action, Phaseolus vulgaris plants were populated with an infested piece of leaf from a mass culture of Tetranychus urticae. The mobile stages which had migrated to the plants were sprayed with the emulsified test preparations from a chromatography atomiser in such a way that the spray broth did not run off. The number of living and dead larvae, adults and eggs was evaluated under a stereoscopic microscope after 2 and 7 days and the result expressed in percentage values. During the test run, the plants stood in greenhouse compartments at 25° C.

In this test, the compounds of Example 1 acted against adults, larvae and eggs of Tetranychus urticae.

EXAMPLE 4: Action against ticks (A) *Rhipicephalus bursa* Five adult ticks and 50 tick larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cottonwool plug and placed on its head to enable the cotton wool to absorb the active substance emulsion. Evaluation of the action against adults was made after 2 weeks and of that against larvae after 2 days. Each test was repeated twice.

(B) *Boophilus microplus* (larvae) Tests were carried out with 20 OP-sensitive and 20 OP-resistant larvae using aqueous emulsions similar to those used in Test A. (The resistance refers to the tolerance towards diazinone). The compounds of Example 1 acted in these tests against adults and larvae of Rhipicephalus bursa and OP-sensitive and OP-resistant larvae of Boophilus microplus.

EXAMPLE 5

(a) Dry cleaning

A 10% solution of a compound of the formula I in methyl cellosolve is prepared. One part by volume of this solution is diluted with 200 parts by volume of a solvent suitable for dry cleaning, for example a suitable petroleum fraction or perchloroethylene. If desired, other cleaning promoters can be added. Woollen articles are then treated in the conventional manner in this cleaning fluid and subsequently centrifuged to a solvent pick-up of about 100% of the wool. After drying, the articles have a moth- and beetle-resistant finish.

In analogous manner, baths of the same or similar composition can also be used for providing untreated or otherwise treated or cleaned articles with a moth- and beetle-resistant finish. Similar mixtures can also be used for spraying or sprinkle wool in any state of processing.

(b) Spraying

A 0.5% solution of an active substance of the formula I in a readily volatile organic solvent is prepared. A woollen article is sprayed with this solution from a conventional spray device so that $2 \times 15$ g/m² of active substance solution is applied, corresponding to a concentration of about 400 ppm on the material at a 30% consumption of the aerosol. The treated woollen fabric has a moth- and beetle-resistant finish.

(c) Pad method

A 4% stock solution in methyl cellosolve of each of the active substances to be tested is prepared. Each stock solution (12.5 ml) is diluted to 50 ml (solution 1) with methyl cellosolve which contains 0.65 g/l of an anionic sulfonated oil. Solution 1 (25 ml) is diluted to 50 ml (solution 2) with methyl cellosolve which contains 0.5 g/l of an anionic sulfonated oil. Solution 2 is then diluted in turn to 50 ml (solution 3) with methyl cellosolve which contains 0.5 g/l of an anionic sulfonated oil.

3 ml of each of solutions, 1, 2 and 3 are poured into crystallisation dishes and a disc of wool flannel is wetted for 3 seconds therein. The moist discs are then padded between aluminium sheets to a pick-up of 50% of each solution. The concentrations of active substance are, respectively, 500 ppm, 250 ppm and 125 ppm for the discs treated with solutions 1, 2 and 3. The moist discs are then dried in the air and subjected to the same biological tests as in the dyebath method.

The compounds of formula I exhibit very good action at concentrations up to 125 ppm against Tineola bisselliella and Tinea pellionella.

(d) Exhaust method

A 0.4% stock solution of each of the active substances of the formula I in methyl cellosolve is prepared. Then a aqueous treatment bath containing, in 120 ml of distilled water, 0.12 ml of Sandozin KB, 0.6 ml of formic acid 1:10 and 0.75 ml of the respective 0.4% stock solution, is prepared at room temperature. Then 3 g of wool flannel are wetted with hot water and put into the bath at room temperature. While constantly circulating the wool sample, the bath temperature is raised to 60° C. in the course of 20 minutes and treatment is carried out for 30 minutes at 60° C. The bath is then cooled, the wool sample rinsed twice for 3 minutes with distilled water, squeezed out by hand and dried in the air. The active substance concentration is 1000 ppm, based on the weight of the wool.

The dried sample is subjected to the moth-proofing test (protection against feeding damage caused by the webbing clothes moth Tineola bisselliella Hum.), in accordance with SNV 195901, and to the resistance test against larvae of the fur beetle (Attagenus piceus olive (black)) and carpet beetle (Anthrenus vorax Waterhouse) in accordance with SNV 195902.

In these tests, 10 larvae of Anthrenus vorax Waterhouse and 10 six- to seven-week-old larvae of Attagenus piceus olive (black) are used. Pieces of the same size are cut out of the treated wool samples and subjected for 14 days at constant temperature (28° C.) and constant relative humidity (65%) to attack (feeding) by 15 larvae of each of the pests. Evaluation is made on the one hand according to the relative loss in weight of the test sample and, on the other, according to the number of still living organisms. The substances of the formula I exhibit very good action against the three pests.

What is claimed is:

1. A cyclopropanecarboxylic acid ester of the formula

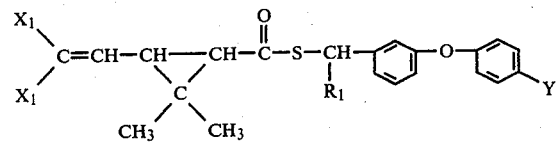

wherein $X_1$ represents fluorine, chlorine or bromine, $R_1$ represents hydrogen, methyl, ethynyl or cyano, and Y represents hydrogen, fluorine, chlorine or bromine.

2. A compound according to claim 1, wherein $X_1$ represents chlorine, and Y represents hydrogen.

3. The compound according to claim 2 of the formula

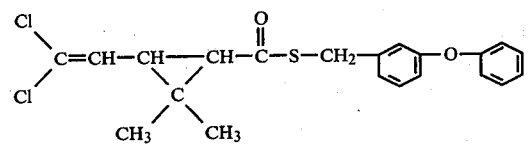

4. A compound of the formula

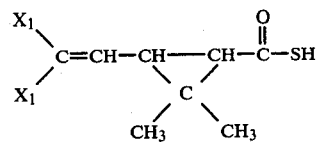

wherein $X_1$ represents fluorine, chlorine or bromine.

5. An insecticidal and acaricidal composition comprising (1) an insecticidally or acaricidally effective amount of a compound according to claim 1 and (2) a carrier.

6. A method for combatting insects and acarids which comprises applying thereto an insecticidally or acaricidally effective amount of a compound of claim 1.

7. A method according to claim 6 in which, in the compound, $X_1$ represents chlorine and Y represents hydrogen.

8. A method for protecting keratinous material against attack by keratin-feeding pests, which method comprises applying to said material, in a protectively effective amount, a compound according to claim 1.

9. A method according to claim 8 in which, in the compound, $X_1$ represents chlorine and Y represents hydrogen.

10. The method according to claim 9 in which the compound is

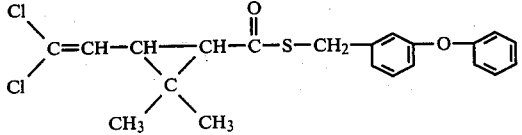

* * * * *